US 8,155,731 B1

(12) United States Patent  (10) Patent No.: US 8,155,731 B1
Bharmi  (45) Date of Patent: Apr. 10, 2012

(54) SYSTEMS AND METHODS FOR DETECTING AND COMPENSATING FOR CHANGES IN POSTURE DURING ISCHEMIA DETECTION USING AN IMPLANTABLE MEDICAL DEVICE

(75) Inventor: Rupinder Bharmi, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 519 days.

(21) Appl. No.: 11/550,751

(22) Filed: Oct. 18, 2006

(51) Int. Cl.
   *A61B 5/0402* (2006.01)
(52) U.S. Cl. ...................................... 600/509
(58) Field of Classification Search .......... 607/9, 17–19; 600/517, 509
   See application file for complete search history.

(56) References Cited

U.S. PATENT DOCUMENTS

| | | | |
|---|---|---|---|
| 4,759,366 A * | 7/1988 | Callaghan ..................... 607/26 |
| 5,113,869 A | 5/1992 | Nappholz et al. |
| 5,135,004 A | 8/1992 | Adams et al. |
| 5,199,428 A | 4/1993 | Obel et al. |
| 5,203,326 A | 4/1993 | Collins |
| 5,313,953 A | 5/1994 | Yomtov et al. |
| 5,328,460 A | 7/1994 | Lord et al. |
| 5,779,645 A | 7/1998 | Olson et al. |
| 5,960,797 A | 10/1999 | Kramer et al. |
| 6,016,443 A | 1/2000 | Ekwall et al. |
| 6,021,350 A | 2/2000 | Mathson |
| 6,104,949 A * | 8/2000 | Pitts Crick et al. ........... 600/547 |
| 6,108,577 A | 8/2000 | Benser |
| 6,112,116 A | 8/2000 | Fischell et al. |
| 6,115,628 A | 9/2000 | Stadler et al. |
| 6,128,526 A * | 10/2000 | Stadler et al. ................. 600/517 |
| 6,377,852 B1 | 4/2002 | Bornzin et al. |
| 6,381,493 B1 * | 4/2002 | Stadler et al. ..................... 607/9 |
| 6,501,983 B1 | 12/2002 | Natarajan et al. |
| 6,516,219 B1 | 2/2003 | Street |
| 6,622,045 B2 | 9/2003 | Snell et al. |
| 6,658,292 B2 | 12/2003 | Kroll et al. |
| 7,181,269 B1 * | 2/2007 | Kroll .............................. 600/517 |
| 7,254,440 B1 * | 8/2007 | Kroll .............................. 600/517 |
| 7,460,906 B2 * | 12/2008 | Libbus ............................. 607/2 |
| 2003/0004549 A1 * | 1/2003 | Hill et al. .......................... 607/9 |
| 2003/0100925 A1 * | 5/2003 | Pape et al. ...................... 607/17 |
| 2004/0049235 A1 * | 3/2004 | Deno et al. ........................ 607/9 |
| 2005/0027323 A1 * | 2/2005 | Mulligan et al. ................ 607/18 |
| 2005/0115561 A1 * | 6/2005 | Stahmann et al. ....... 128/200.24 |
| 2005/0149133 A1 * | 7/2005 | Libbus et al. ..................... 607/9 |
| 2005/0288600 A1 * | 12/2005 | Zhang et al. .................. 600/510 |
| 2006/0069322 A1 | 3/2006 | Zhang et al. |
| 2006/0253043 A1 * | 11/2006 | Zhang et al. .................. 600/512 |

(Continued)

OTHER PUBLICATIONS

Jones, Alice Y.M. PT, PhD et al., "Body position change and its effect on hemodynamic and metabolic status," Heart Lung 2004;33: 281-90.

(Continued)

*Primary Examiner* — Niketa Patel
*Assistant Examiner* — Hiba El-Kaissi

(57) ABSTRACT

Techniques are described for detecting changes in posture; detecting cardiac ischemia while accounting for changes in posture; and delivering therapy or warning signals in response thereto using the implantable medical device. In one example, the device detects variations in the electrical cardiac signals indicative of a possible episode of cardiac ischemia. Changes in patient posture are detected as well using an accelerometer or similar device. Then, an episode of cardiac ischemia is detected based on the variations in the cardiac signals while distinguishing variations due to changes in posture. In another example, the device instead detects changes in posture based on transient changes in morphological features of electrical cardiac signals.

16 Claims, 8 Drawing Sheets

U.S. PATENT DOCUMENTS

| | | | |
|---|---|---|---|
| 2006/0253164 A1* | 11/2006 | Zhang et al. | 607/28 |
| 2007/0179392 A1* | 8/2007 | Zhang | 600/512 |
| 2007/0260285 A1* | 11/2007 | Libbus et al. | 607/9 |
| 2007/0299476 A1* | 12/2007 | Park et al. | 607/9 |
| 2008/0004667 A1* | 1/2008 | Arcot-Krishnamurthy et al. | 607/17 |

OTHER PUBLICATIONS

Yeragani, Vikram K. et al., "Effect of Posture and Isoproterenol on Beat-to-Beat Heart Rate and QT Variability," Neuropsychobiology 2000;41: 113-123.

NonFinal Office Action, mailed Feb. 4, 2009: Related U.S. Appl. No. 11/550,744.
Final Office Action, mailed Jul. 16, 2009: Related U.S. Appl. No. 11/550,744.
Final Office Action, mailed Jul. 6, 2009—Related U.S. Appl. No. 11/550,744.
Advisory Action, mailed Sep. 30, 2009—Related U.S. Appl. No. 11/550,744.
Advisory Action, mailed Sep. 25, 2009—Related U.S. Appl. No. 11/550,744.
NonFinal Office Action, mailed Jan. 12, 2010—Related U.S. Appl. No. 11/550,744.

* cited by examiner

SYSTEMS AND METHODS FOR DETECTING AND COMPENSATING FOR CHANGES IN POSTURE DURING ISCHEMIA DETECTION USING AN IMPLANTABLE MEDICAL DEVICE

CROSS-REFERENCE TO RELATED APPLICATIONS

In This application is related to copending U.S. patent application Ser. No. 11/550,774, file concurrently herewith, titled "Systems and Methods for Detecting and Compensating for Changes in Posture During Ischemia Detection Using an Implantable Medical Device".

FIELD OF THE INVENTION

The invention generally relates to implantable medical devices such as pacemakers and implantable cardioverter/defibrillators (ICDs) and, in particular, to (1) techniques for detecting changes in posture and also to (2) techniques for compensating for changes in posture during detection of cardiac ischemia or other medical conditions.

BACKGROUND OF THE INVENTION

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within twenty-four four hours, sometimes within only a half an hour or less. Accordingly, it would be highly desirable to provide a technique for reliably detecting episodes of acute myocardial ischemia so that the victim may be warned and medical attention sought. If properly warned, surgical procedures may be implemented to locate and remove the growing arterial blockage or anti-thrombolytic medications may be administered. At the very least, advanced warning would allow the victim to cease activities that might result in a fatal accident. Moreover, in many cases, AMI or VF is triggered by strenuous physical activities and so advanced warning would allow the victim to cease such activities, possibly preventing AMI or VF from occurring.

Many patients at risk of cardiac ischemia have pacemakers, ICDs or other medical devices implanted therein. Accordingly, techniques have been developed for detecting cardiac ischemia using implanted medical devices. In particular, techniques have been developed for analyzing intracardiac electrogram (IEGM) signals in an effort to detect cardiac ischemia. See, as examples, the following U.S. Pat. No. 5,113,869 to Nappholz; U.S. Pat. No. 5,135,004 to Adams et al.; U.S. Pat. No. 5,199,428 to Obel et al.; U.S. Pat. No. 5,203,326 to Collins; U.S. Pat. No. 5,313,953 to Yomtov et al; U.S. Pat. No. 6,501,983 to Natarajan, et al.; U.S. Pat. Nos. 6,016,443, 6,233,486, 6,256,538, and 6,264,606 to Ekwall; U.S. Pat. No. 6,021,350 to Mathson; U.S. Pat. Nos. 6,112,116 and 6,272,379 to Fischell et al; U.S. Pat. Nos. 6,128,526, 6,115,628 and 6,381,493 to Stadler et al; and U.S. Pat. No. 6,108,577 to Benser. Many ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). The QRS complex usually follows an atrial depolarization (also referred to as a P-wave.) Strictly speaking, P-waves, R-waves and T-waves are features of a surface electrocardiogram (EKG). For convenience and generality, herein the terms R-wave, T-wave and P-wave are used to refer to the corresponding internal signal component as well.

Alternative techniques for detecting cardiac ischemia have also been developed that do not necessarily rely on ST segment elevation. One such technique is set forth in U.S. patent application Ser. No. 10/603,429, entitled "System And Method For Detecting Cardiac Ischemia Using An Implantable Medical Device," of Wang et al., filed Jun. 24, 2003, which is incorporated by reference herein. Rather than examine the ST segment, the technique of Wang et al. instead examines post-T-wave segments, i.e. that portion of the cardiac signal immediately following the T-wave. In one example, the onset of cardiac ischemia is identified by detecting a sharp falling edge within post-T-wave signals. Another technique for detecting cardiac ischemia based on T-waves is set forth in U.S. patent application Ser. No. 10/603,398, entitled "System And Method For Detecting Cardiac Ischemia Based On T-Waves Using An Implantable Medical Device," of Min et al., filed Jun. 24, 2003. With the technique of Min et al., cardiac ischemia is detected based either on the total energy of the T-wave or on the maximum slope of the T-wave. See, also, U.S. patent application Ser. No. 11/043,612, of Kil et al., filed Jan. 25, 2005, entitled "System and Method for Distinguishing Among Ischemia, Hypoglycemia and Hyperglycemia Using an Implantable Medical Device." In addition, see U.S. patent application Ser. No. 11/394,724, of Ke et al. entitled "System and Method for Detecting Cardiac Ischemia in Real-Time using a Pattern Classifier Implemented within an Implantable Medical Device".

Thus, a variety of techniques have been developed for detecting cardiac ischemia based on changes in IEGM morphology. However, it can sometimes be difficult to distinguish variations in IEGM morphology caused by cardiac ischemia from variations due to changes in patient posture. In this regard, various gravity-dependent and position-based hemodynamic and pulmonary affects on heart rate, blood pressure and oxygen consumption have been documented. See, Jones et al., "Body Position Change and Its Effect on Hemodynamic and Metabolic Status," Heart Lung. 2004 September-October; 33(5):281-90. Jones et al. report that heart rate, blood pressure and oxygen consumption are highest in the sitting position compared to the lying (supine) positions and lowest in the left side lying position. Changes in these parameters can potentially affect IEGM morphology. Also, it has been reported that patient posture can affect QT variability (where QT variability refers to a beat-to-beat variability in the duration of the interval between the Q-point of a QRS complex and the subsequent T-wave.) See, Yeragani et al., "Effect Of Posture and Isoproterenol on Beat-To-Beat Heart Rate and QT Variability," Neuropsychobiology. 2000; 41(3):113-23. In particular, Yeragani et al. found that the QT variability index is significantly higher in the standing that in the supine posture.

Moreover, the present inventor and her colleagues have observed that an atrial paced depolarization integral (PDI) varies due to patient posture. Atrial PDI is a well-known parameter derived from an integral of certain morphological features of the IEGM derived from a paced atrial beat. (For a description of PDI, also sometimes referred to as a depolarization gradient, see U.S. Pat. No. 4,759,366, to Callaghan.) In one example, atrial PDI was derived for ten patients under three different body positions: supine, right-side lying and left-side lying. It was observed that when the patient was first in the supine position and then switched to the right side lying position, the mean of the atrial PDI decreased by 5.6±8.9%. The standard deviation of the atrial PDI decreased by 36.8±7.3%. Similarly, when the patient was first in the supine position, and then switched to the left side lying position, the mean of the atrial PDI decreased by 1.6±3.5%, and the standard deviation decreased by 52.2±29%. In other words, baseline values of atrial PDI can vary depending upon patient posture. In addition to changes in baseline values, transient changes also occur while the patient changes from one posture or body position to another.

Hence, changes in patient posture can affect metrics derived from IEGM morphology and can thereby potentially affect the reliability of IEGM-based cardiac ischemia detection. Accordingly, it would be desirable to provide techniques for improving the reliability and specificity of ischemia detection by accounting for changes in posture and it is to this end that aspects of the present invention are directed. Posture changes can also potentially affect the detection of other medical conditions besides ischemia and so aspects of the invention are also directed to that end as well. It would also be desirable to provide new and improved techniques for detecting the actual changes in posture and still other aspects of the invention are directed to that end.

SUMMARY OF THE INVENTION

In one example, a method is provided for use with an implantable medical device for implant within a patient for improving the specificity of the detection of cardiac ischemia or other medical conditions. Briefly, electrical cardiac signals are detected within the patient and variations in the cardiac signals indicative of a possible episode of a medical condition are identified. Changes in patient posture are detected as well, typically using an accelerometer or similar device. Then, an episode of cardiac ischemia or other medical condition is detected based on the variations in the cardiac signals while distinguishing variations due to changes in posture. In one particular example, any cardiac signals detected during the change in posture are excluded for the purposes of ischemia detection so that transient morphological variations caused by posture change do not trigger a false positive. Preferably, cardiac signals detected just following the change in posture are excluded as well, as any transient variations in the cardiac signals may not completely subside until after the change in posture is completed. Typically, any cardiac signals not excluded due to changes in posture are analyzed by the implanted device to extract morphological parameters such as ST segment elevation, which are then exploited to detect cardiac ischemia or other medical conditions.

Upon detecting of an episode of cardiac ischemia, appropriate warning signals are generated, which can include both "tickle warning" signals applied to subcutaneous tissue and short range telemetry warning signals transmitted to a device external to the patient. In one example, once the tickle warning is felt, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal.

Therapy may also be applied or modified by the implanted system in response to cardiac ischemia, depending upon the capabilities of the system. For example, if the implanted system is equipped with a drug pump, appropriate medications may be administered such as anti-thrombolytic drugs. If overdrive pacing is being applied by the system, overdrive pacing is preferably deactivated to prevent the increased heart rate associated with overdrive pacing from exacerbating the ischemia. If the system has defibrillation capabilities, the system may immediately begin charging defibrillation capacitors upon detection of cardiac ischemia to permit prompt delivery of a defibrillation shock if the ischemia triggers VF. Additionally, or in the alternative, diagnostic information pertaining to ischemia may be stored for subsequent review by a physician.

In another example of the invention, a method is provided for use with an implantable medical device for detecting changes in posture in a patient in which the device is implanted based on electrical cardiac signals. That is, rather than detecting changes in posture using an accelerometer or other motion sensitive device, the implantable medical device detects changes in posture directly from the cardiac signals. Briefly, morphological features of cardiac electrical signals affected by patient posture are detected. Changes in patient posture are then detected based on transient variations in the morphological features. The cardiac signal-based change of posture detection technique may be advantageously employed within devices not equipped to detect posture changes using accelerometers or may be used to corroborate the detection of a change in posture.

In one particular example, the implanted device measures atrial PDI for the purposes of detecting changes in posture. In the example, the implanted device determines a baseline PDI level (such as the mean or average of the PDI) then detects any significant transient variations in PDI. The device also determines the baseline PDI level following the significant variations in PDI. A change in posture is deemed to have occurred if the baseline PDI level following the transient variations in PDI differs significantly from the baseline level prior to the transient variations. In one example, a change of posture is detected by observing (1) significant transient variations in PDI (caused by the movement of the patient from one posture to another), (2) a change in baseline PDI (caused by gravity-dependent and position-based hemodynamic and pulmonary affects associated with the new posture) and (3) a change in standard deviation of the PDI or peak-to-peak variability of the PDI (caused by gravity-dependent and position-based hemodynamic and pulmonary affects associated with the new posture.) Preferably, the device also detects the gradually decay of the transient variations following the change in posture. The observation of such a gradual decay helps confirm that the transient variations were due to a change in posture rather than to some other factor, such as an episode of cardiac ischemia. The change in posture can be further corroborated by observing associated variations in one or more of heart rate, blood pressure and oxygen consumption.

Thus, techniques are provided for improving the specificity of IEGM-based techniques for detecting cardiac ischemia or other medical conditions by taking into account changes in posture. Techniques are also provided for detecting changes in posture directly from IEGMs. The IEGM-based change of posture detection techniques may be used in connection with the ischemia detection techniques or for other purposes.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
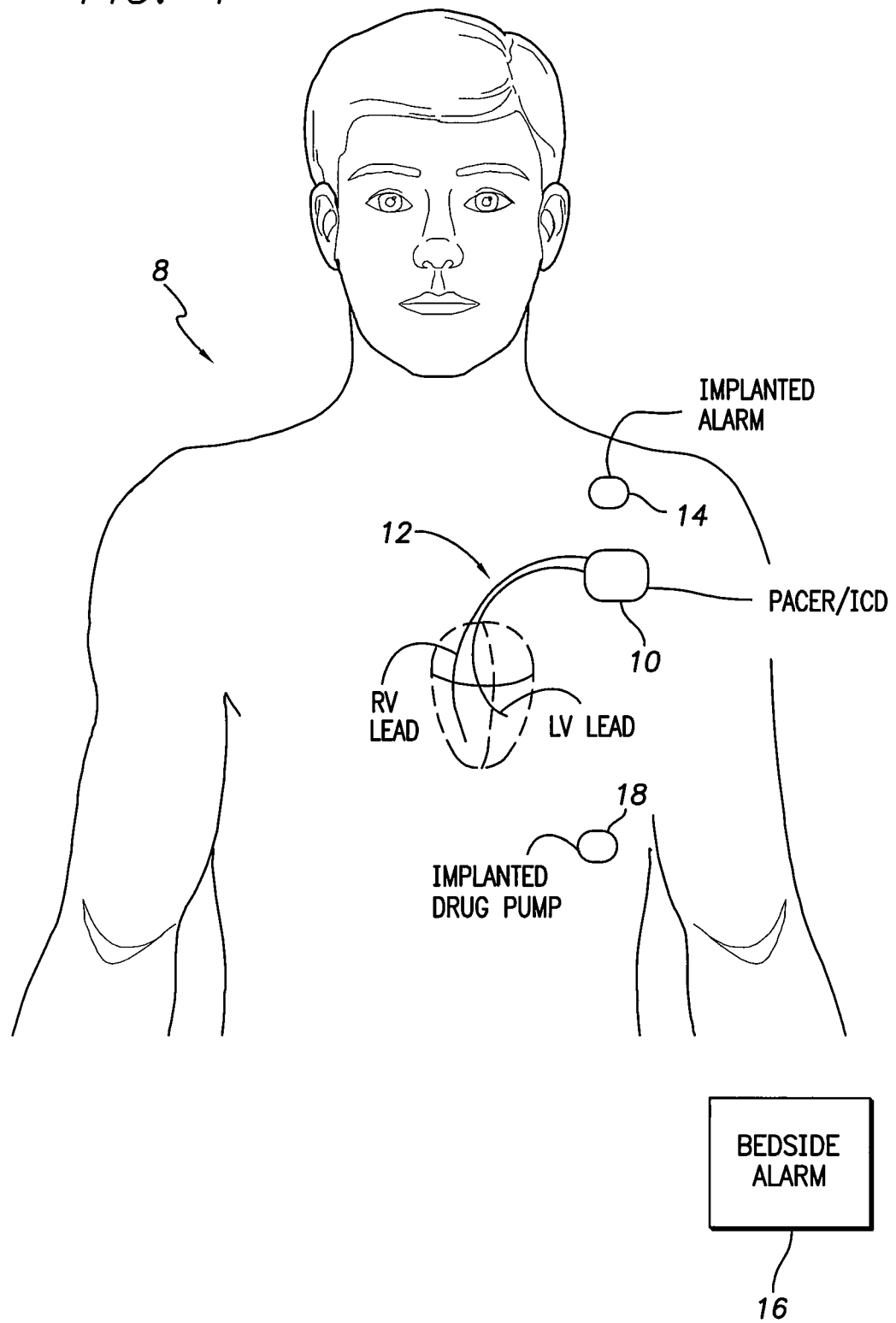
FIG. 1 illustrates pertinent components of an implantable medical system having a pacer/ICD capable of: detecting changes in posture; detecting cardiac ischemia while accounting for changes in posture; and delivering therapy or warning signals in response thereto.
Figure 7:
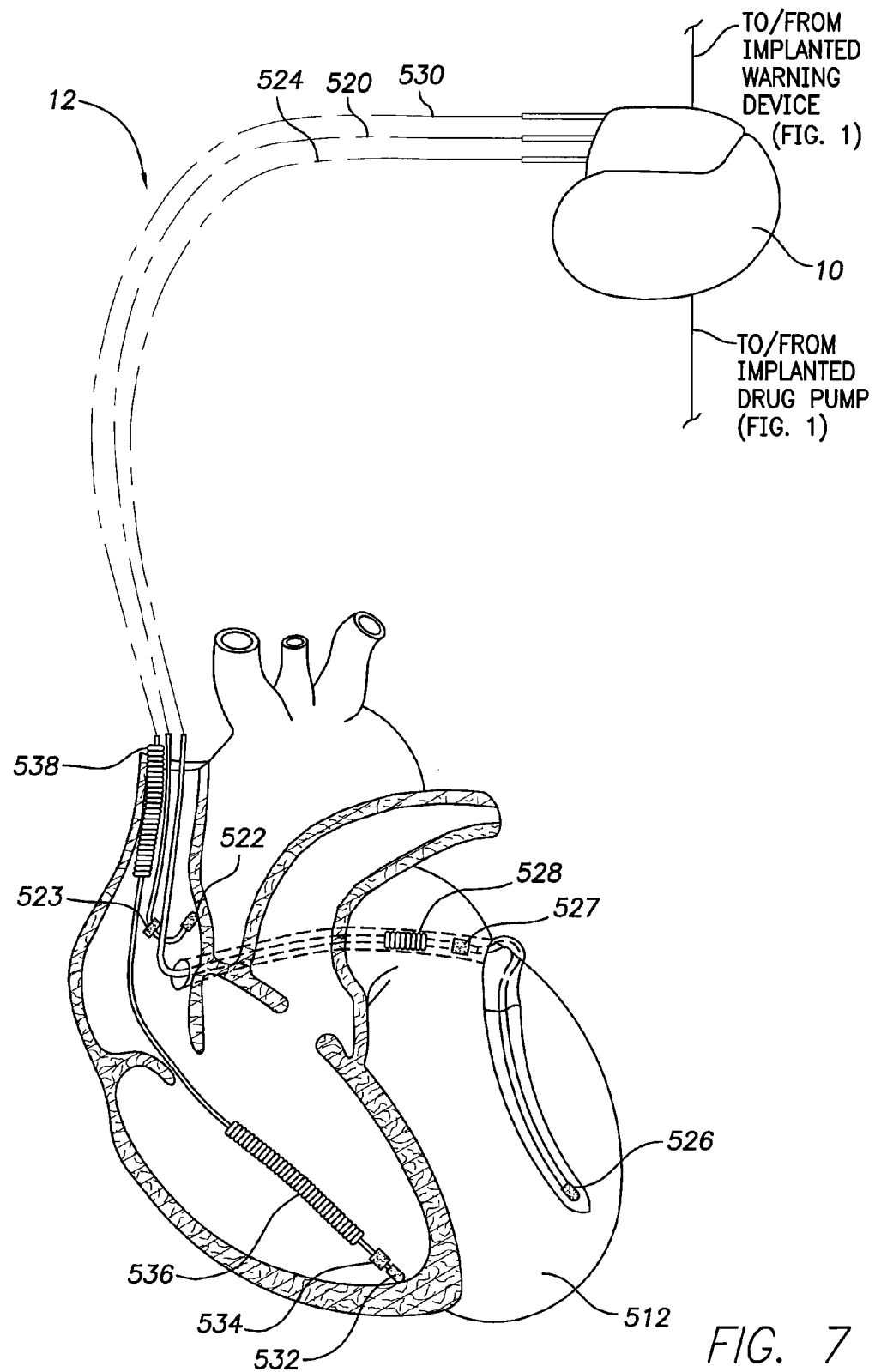
FIG. 7 is a simplified, partly cutaway view, illustrating the pacer/ICD of FIG. 1 along with a complete set of leads implanted in the heart of a patient.

FIG. 1 illustrates an implantable medical system 8 having a pacer/ICD capable of detecting changes in posture; detecting cardiac ischemia while accounting for changes in posture; and delivering therapy or warning signals in response thereto. To this end, pacer/ICD 10 receives voltage signals from various cardiac pacing leads (only two of which are shown in the FIG. 1) from which various channels of IEGM signals are derived including, for example, unipolar or bipolar A-IEGM signals and unipolar or bipolar V-IEGM signals. A complete set of exemplary pacing leads are shown in FIG. 7 from which a wide variety of specific channels of IEGM signals may be derived.

Figure 2:
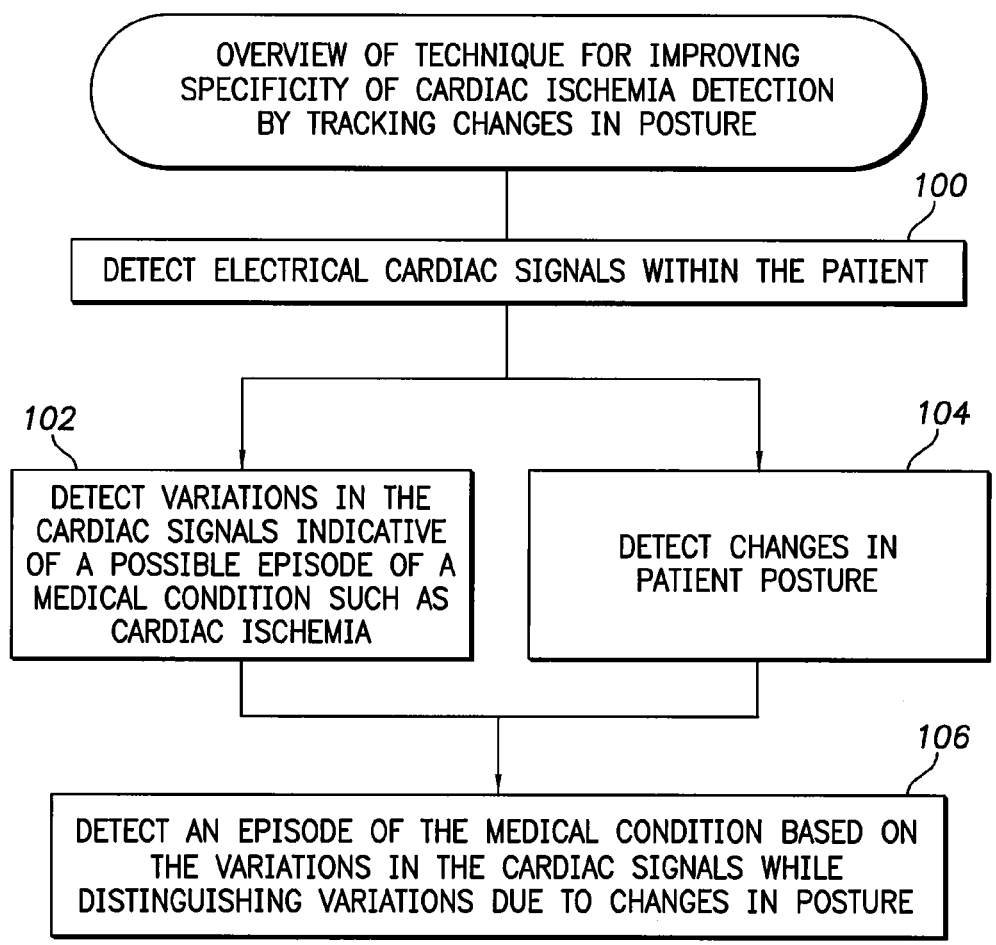
FIG. 2 provides an overview of an exemplary technique, which may be performed by the system of FIG. 1, for detecting cardiac ischemia or other medical conditions based on IEGM signals while accounting for changes in posture.
Figure 3:
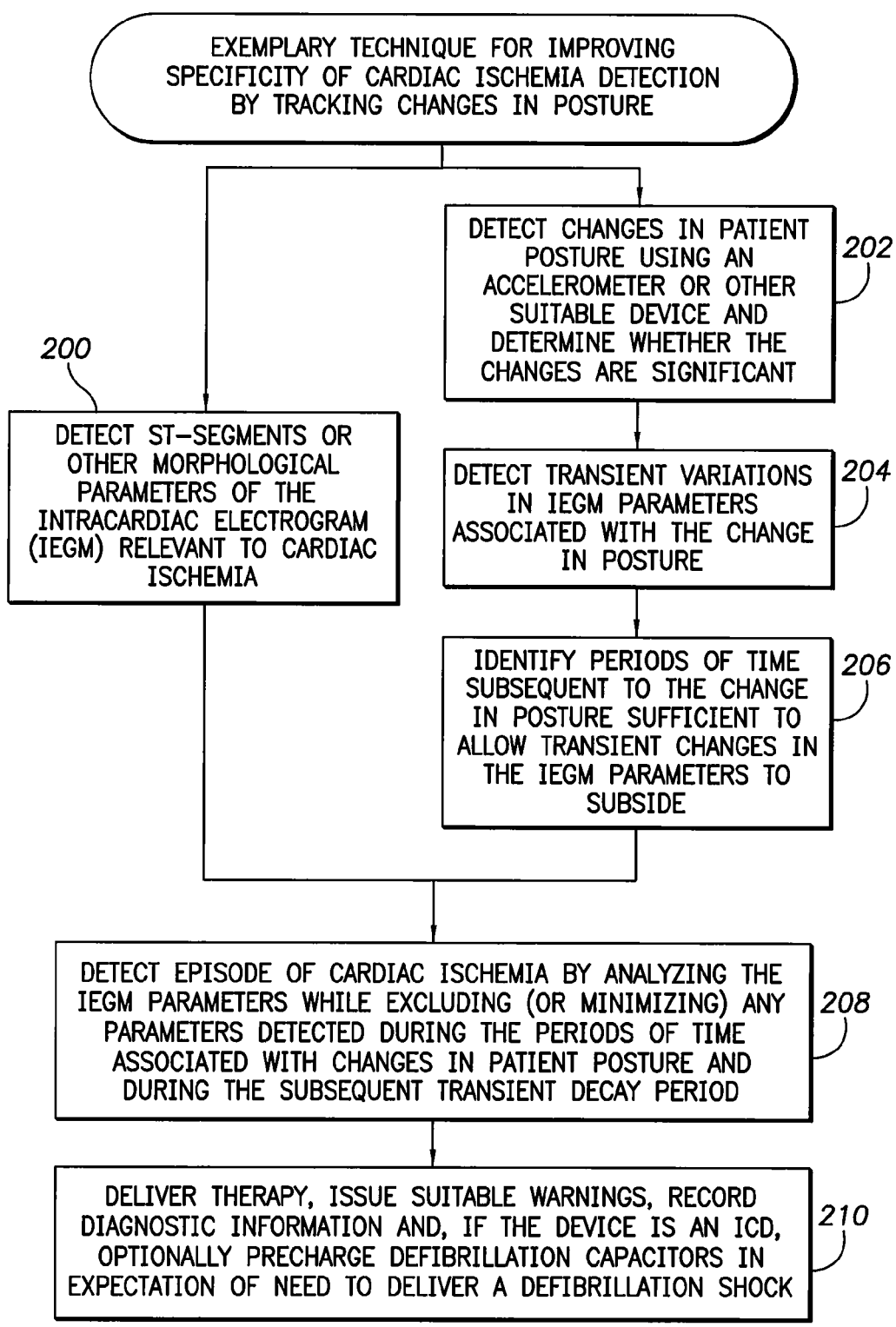
FIG. 3 illustrates a particular example of the ischemia detection technique of FIG. 2.
Figure 4:
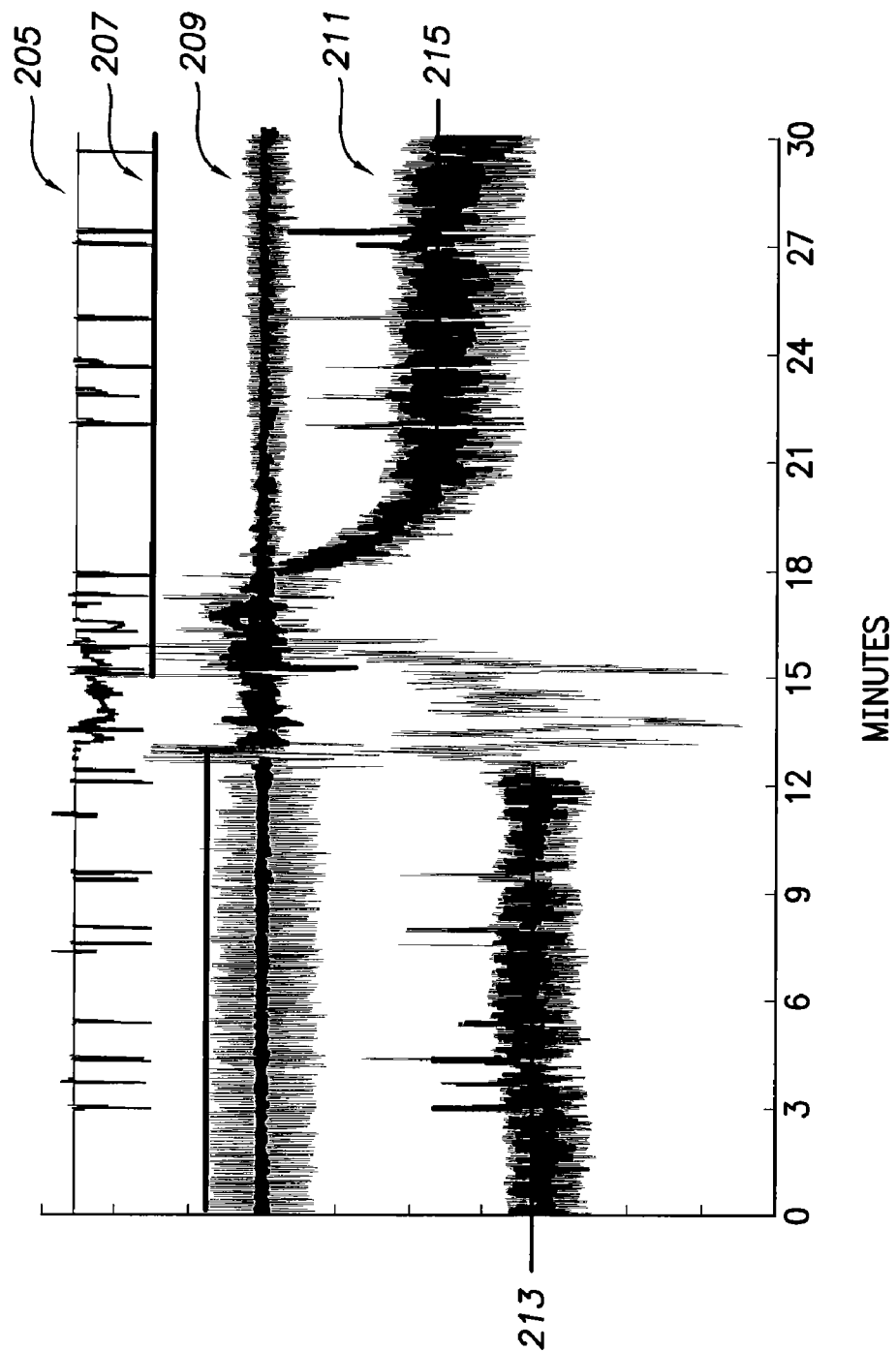
FIG. 4 is a graph illustrating the affects of posture change on various exemplary cardiac and respiratory parameters.

In one embodiment, described primarily with reference to FIGS. 2-4, the pacer/ICD continuously examines the IEGM signals for an indication of the onset of an episode of cardiac ischemia, such as by detecting certain changes in ST segment elevation indicative of ischemia. Simultaneously, the pacer/ICD examines signals received from an accelerometer (which may be an internal component of the pacer/CID) to detect changes in posture. That is, the pacer/ICD uses the accelerometer to detect when the patient rises from a seated posture to a standing posture, or when the patient rolls over from a left-side lying (LSL) to a right-side lying (RSL) posture, etc. Since changes in posture can cause transient changes in IEGM that might cause a false positive ischemia detection, the pacer/ICD excludes any IEGM signals detected during (and shortly following) a change in posture. In this manner, the pacer/ICD achieves greater specificity in detecting actual episodes of cardiac ischemia. This general technique can also be applied to detecting other medical conditions based on IEGM signals where changes in posture can affect the reliability of the detection procedure.

If an episode of cardiac ischemia is detected, the pacer/ICD uses additional implanted components (if so equipped) to deliver appropriate therapy or warning signals. For example, the pacer/ICD may activate an internal alarm 14 or an external bedside alarm 16. Internal alarm 14 may be a vibrating device or a "tickle" voltage device that, in either case, provides perceptible stimulation to the patient to alert the patient to the episode of ischemia. The bedside alarm may provide audible or visual alarm signals of sufficient magnitude to alert the patient. If an activity sensor is provided within the pacer/ICD, the form of the alarm may be controlled based on patient activity. For example, if the activity level indicates that the patient is asleep, a more noticeable alarm may be employed than if the patient is deemed to be awake. In addition, while the patient is asleep, the intensity of the alarm signal can be periodically increased until the patient awakens, as detected by the activity sensor. Warning signals may be relayed from the bedside alarm to a physician or other medical professional via a communication network. A system incorporating bedside monitoring units connected to a centralized external programmer system is described in U.S. Pat. No. 6,622,045 to Snell et al., "System and Method for Remote Programming of Implantable Cardiac Stimulation Devices". Additionally, or in the alternative, the system may include a drug pump 18 capable of the delivering medications in an attempt to mitigate the episode of ischemia. If overdrive pacing is being applied by the system, overdrive pacing is preferably deactivated to prevent the increased heart rate associated with overdrive pacing from exacerbating the ischemia. If the system has defibrillation capabilities, the system may immediately begin charging defibrillation capacitors upon detection of cardiac ischemia to permit prompt delivery of a defibrillation shock if the ischemia triggers VF.

Figure 5:
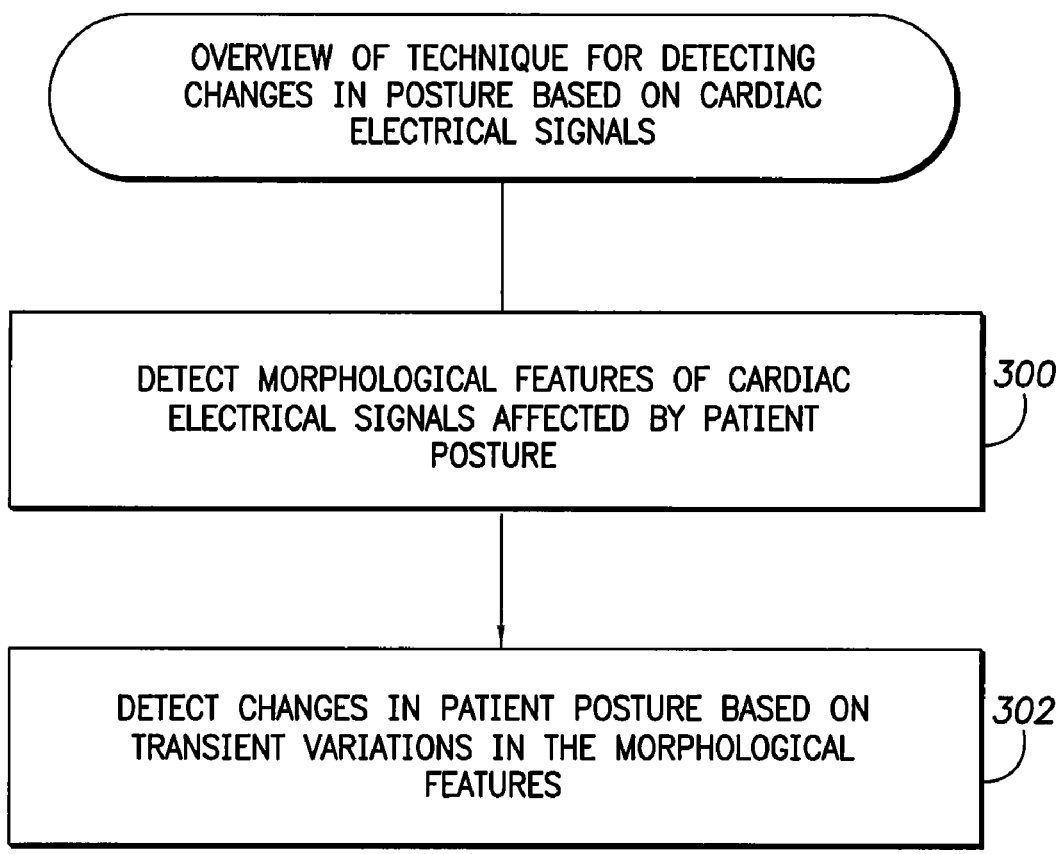
FIG. 5 provides an overview of an exemplary technique, which may also be performed by the system of FIG. 1, for detecting a change in posture based on IEGM signals.
Figure 6:
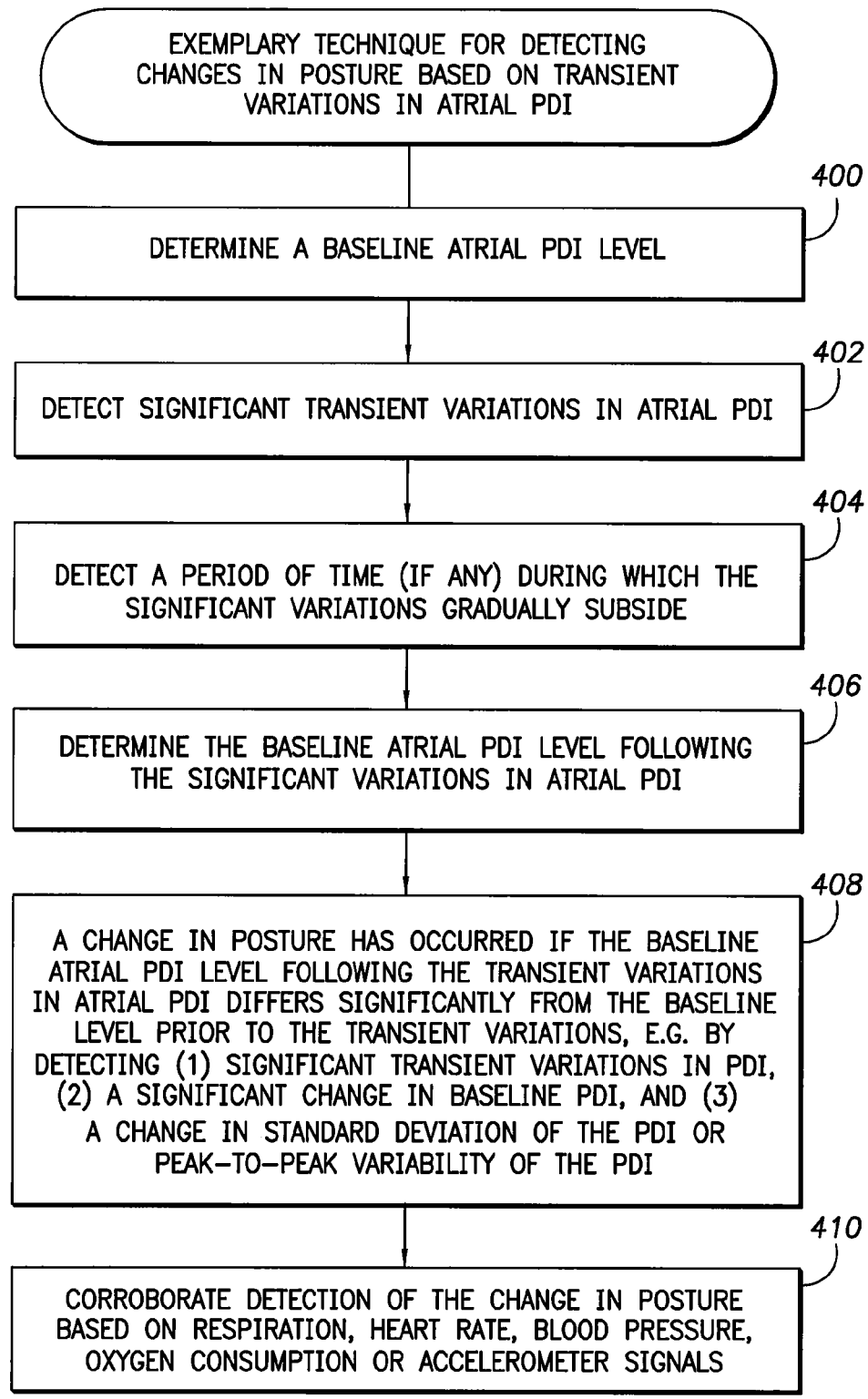
FIG. 6 illustrates a particular example of the exemplary posture change detection technique of FIG. 5.

In another embodiment, described primarily with reference to FIGS. 5-6, the pacer/ICD additionally or alternatively detects the actual changes in posture based on the IEGM signals. That is, rather than use an accelerometer to detect changes in posture, the pacer/ICD examines the IEGM signals for an indication of a change in posture, such as by detecting certain changes in atrial PDI values indicative of posture changes. Depending upon the programming of the pacer/ICD, the device can use the detection of posture change to exclude IEGM signals for the purposes of cardiac ischemia detection (using the techniques of FIGS. 2-4.) However, the IEGM-based change of posture detection can additionally or alternatively be used for other purposes as well, such as to control or modify delivery of pacing therapy and the like. For example, the pacing rate may be increased following a sudden change in posture from sitting to standing so as to prevent blood pressure from dropping within the patient, which might cause the patient to become dizzy.

Thus, FIG. 1 provides an overview of an implantable system for detecting changes in posture; detecting cardiac ischemia while accounting for changes in posture; and delivering therapy or warning signals in response thereto. Although a pacer/ICD is illustrated in FIG. 1, it should be understood that the detection techniques of the invention may be implemented within other implantable medical devices. Note also that internal signal transmission lines for interconnecting the various implanted components are not shown. Alternatively, wireless signal transmission may be employed. In addition, it should be appreciated that systems provided in accordance with invention need not include all the components shown in FIG. 1. In many cases, for example, the system will include only the pacer/ICD and its leads. Other implementations will employ internal or external alarms but no drug pump. These are just a few exemplary embodiments. No attempt is made herein to describe all possible combinations of components that may be provided in accordance with the general principles of the invention. Also, note that the particular locations of the implanted components are merely exemplary.

Cardiac Ischemia Detection

FIG. 2 provides an overview of the techniques of the invention for improving the specificity of cardiac ischemia detection by tracking and recognizing changes in posture. At step 100, the pacer/ICD detects electrical cardiac signals within the patient, such as IEGM signals. Otherwise conventional techniques may be used for converting voltage signals sensed using the various leads into IEGM or similar signals. At step 102, the pacer/ICD detects variations in the IEGM signals indicative of a possible episode of cardiac ischemia. For example, deviations in ST segment elevation may be detected, alone or in combination with other morphological parameters affected by ischemia. Specific examples of IEGM-based ischemia detection techniques are listed above in the Summary. Contemporaneously, at step 104, the pacer/ICD detects changes in patient posture, such as a change from LSL to RSL, from sitting to standing, or from supine to prone, etc. In general, any suitable posture change detection technique may be exploited based, for example, on signals from a 3-D accelerometer. Some particularly effective techniques are described in U.S. Pat. No. 6,658,292 of Kroll et al., entitled "Detection of Patient's Position and Activity Status Using 3D Accelerometer-Based Position Sensor". See, also, U.S. patent application Ser. No. 10/329,233, of Koh et al., entitled "System and Method for Determining Patient Posture Based On 3-D Trajectory Using an Implantable Medical Device," filed Dec. 23, 2002. Preferably, only significant changes in posture are detected, particularly changes in posture that result in a different orientation of the torso relative to gravity, such as a change from LSL to RSL or from supine to prone, etc, as these changes are most likely to affect the IEGM parameters relevant to ischemia detection. In one example, the amount of posture change is evaluated and compared against a threshold indicative of a significant posture change. In this manner, slight changes in posture corresponding to slight changes in body orientation are ignored.

At step 106, the pacer/ICD then detects an episode of the cardiac ischemia based on the variations in the cardiac signals while distinguishing variations due to changes in posture. In one example, to be described in detail with reference to FIG. 3, the pacer/ICD ignores or excludes any IEGM data detected during and shortly after the posture change for the purposes of ischemia detection. (The IEGM data is still processed by the device for all other purposes such as for controlling the delivery of pacing pulses, detecting tachyarrhythmias, etc.)

By excluding IEGM data detected during and shortly after the change in posture, transient changes in the IEGM caused by the change in posture are thereby prevented from triggering false positive ischemia detections. In other examples, however, other techniques may be employed for distinguishing the posture change for the purposes of ischemia detection. For example, if a particular change in posture is known to consistently produce a certain affect on IEGM morphological parameters (such as a certain change in ST segment elevation), the morphological parameters may be adjusted to compensate for the change in posture for the purposes of ischemia detection. In this manner, certain morphological parameters detected during certain changes in posture may still be employed in the detection of ischemia. Otherwise routine experimentation may be performed to identify particular morphological parameters and/or particular changes in posture for which this may be applicable. Exemplary techniques for detecting and evaluating morphological features of the IEGM are described in: U.S. Pat. No. 5,779,645 to Olson, et al. entitled "System and Method for Waveform Morphology Comparison" and U.S. Pat. No. 6,516,219 to Street, entitled "Arrhythmia Forecasting Based on Morphology Changes in Intracardiac Electrograms".

Although described with reference to detection of ischemia, the general technique of FIG. 2 may be applied for use with the detection of other medical conditions. In general, the techniques of the invention may be advantageously exploited in connection with any disorder that can be detected based on an analysis of IEGM morphological parameters that are, in turn, affected by changes in posture. Examples include detection of hyperglycemia and hypoglycemia. See, e.g., the Kil et al. and Ke et al. patent applications cited above. See, also, U.S. patent application Ser. No. 11/117,624, of Bharmi, filed Apr. 28, 2005, entitled "System and Method for Detecting Hypoglycemia based on a Paced Depolarization Integral Using an Implantable Medical Device".

FIGS. 3 and 4 illustrate an example of the general technique of FIG. 2. Beginning at step 200, the pacer/ICD detects ST-segments or other morphological parameters of the IEGM relevant to cardiac ischemia, such as one or more of the elevation, width, maximum slope, and peak amplitude of P-waves, QRS-complexes, T-waves and the various intervals therebetween (such as R-R, P-P), as well as integrals thereof such as aPDI, vPDI, far field PDI (ffPDI) and other parameters such as transform length (tl), fast Fourier transform length (fftl), etc. Contemporaneously, at step 202, the pacer/ICD detects changes in patient posture using a 3D accelerometer or other suitable device and also determines whether the changes are significant (using, e.g., suitable thresholds). As already noted, changes in posture that are not significant can typically be ignored, as such changes do not significantly affect ischemia detection. At step 204, the pacer/ICD detects transient variations in IEGM morphological parameters associated with the change in posture, i.e. the pacer/ICD identifies transient changes that occurred while the patient was actually moving from one posture to another. Parameters detected during the actual change in posture are the most suspect for the purposes of ischemia detection. At step 206, the pacer/ICD also identifies periods of time subsequent to the change in posture sufficient to allow transient the changes detected at step 204 to subside or decay.

FIG. 4 illustrates the affect on various IEGM morphological parameters and other parameters during a change in posture. More specifically, FIG. 4 illustrates R-R interval 205 (i.e. the interval between successive R-waves or QRS-complexes), body position 207 as determined by an accelerometer, respiration 209 and atrial PDI 211. Note that the respiration graphs include gray lines representing respiration as determined by an external chest sensor as well as darker lines representing respiration as determined by an external nasal flow sensor. In this example, the patient was initially supine, then made a quick change to RSL, then LSL, then back to RSL and then remained in the RSL posture. These movements occurred during minutes 12 to 15. As can be seen, the change in posture causes significant transient variations in both R-R interval and atrial PDI. Although not explicitly shown in the figure, it is believed that similar transient variations may also arise in ST segment elevation or in other morphological parameters relevant to cardiac ischemia detection. Furthermore, as can be seen, the transient variations do not subside until well after the change in posture has been completed, likely due to gradual hemodynamic and pulmonary compensatory effects. It is this latter period of time that is detected at step 206 of FIG. 3.

Returning to FIG. 3, at step 208, the pacer/ICD detects the episode of cardiac ischemia by analyzing the IEGM parameters while excluding (or minimizing the weight of) any parameters detected during the periods of time associated with changes in patient posture (detected at steps 202 and 204) and during the subsequent transient decay period (detected at step 206). In one example, the pacer/ICD simply ignores all IEGM parameters detected during these intervals of time for the purposes of ischemia detection. In other examples, the pacer/ICD "weights" these parameters less heavily than other parameters for the purposes of ischemia detection. The choice may depend upon the particular technique used to detect ischemia. For example, when using the pattern classifier techniques of the Ke et al. patent application cited above, it may be appropriate to adjust the weight of the parameters rather than merely to exclude the parameters. In any case, by excluding or minimizing the weight of parameters affected by changes in posture, false positive ischemia detection is avoided thereby improving detection specificity. Note also that, rather than specifically detecting the gradual decay in transients at step 206, the pacer/ICD can instead be programmed simply to employ a fixed time interval. That is, upon detecting a significant change in posture, the pacer/ICD excludes any IEGM parameters detected during some predetermined interval of time (such as five minutes) following the change in posture. As can be appreciated, a variety of specific techniques may be employed consistent with the general principals of the invention.

Note also that, in the example of FIG. 4, the average (i.e. baseline) level 213 of atrial PDI before the change of posture differs from the average PDI 215 following the change in posture, likely due to the difference between the starting posture and the final posture. Depending upon the particular technique used to detect ischemia, it may be desirable to compensate for changes in baseline by normalizing IEGM data. In one example, a running average of the mean and the standard-deviation of a particular IEGM parameter are maintained with a window of width equal to 64 beats, i.e. i–64 to i+64. An i+64 scheme is preferable to using an i–128 to i scheme to prevent lag due to such calculation. The IEGM parameters are then normalized by eliminating any variation in the calculated mean and standard deviation. In one specific example, the following formula is used:

$$x'_i = \frac{x_i - \mu}{\sigma} i \in N$$

where μ=local mean, x represents the parameter to be normalized, σ represents a local standard deviation. In this manner, a moving window normalization is exploited to remove the mean and standard deviation changes that occur due to body position changes while retaining variations due to ischemia. (See, also, U.S. patent application Ser. No. 11/416,317, filed May 1, 2006, entitled "System And Method For Detecting Abnormal Respiration Via Respiratory Parameters Derived From Intracardiac Electrogram Signals," which applies similar normalization procedures in the detection of patient respiration from IEGM signals.) Any data excluded from ischemia detection due to changes in posture is likewise excluded during normalization. That is, only relatively stable data detected while the patient is not changing posture is normalized via this formula.

Finally, with regard to FIG. 3, at step 210, the pacer/ICD then delivers therapy, issues suitable warnings, records diagnostic information and, if the device is an ICD, optionally precharges defibrillation capacitors in expectation of the need to deliver a defibrillation shock to address VF that might be triggered by the ischemia. For example, if a drug pump is implanted within the patient, the pump may be controlled to deliver suitable anti-thrombolytic medications directly to the patient. Implantable devices for delivering anti-thrombolytic drugs are discussed in U.S. Pat. No. 5,960,797 to Kramer, et al. Implantable drug pumps are also discussed in U.S. Pat. No. 5,328,460 to Lord, et al., entitled "Implantable Medication Infusion Pump Including Self-Contained Acoustic Fault Detection Apparatus". The device may also change pacing parameters in response to the detection of ischemia to, for example, deactivate overdrive pacing, which may exacerbate the ischemia. Other forms of elevated pacing may be discontinued as well, such as atrial fibrillation (AF) suppression therapy or activity-based rate responsive pacing. Various techniques for controlling delivery of therapy in response to ischemia are discussed U.S. Pat. No. 6,256,538 to Ekwall, listed above. See also U.S. Pat. No. 6,377,852 to Bornzin et al., which provides techniques for slowing the heart rate in response to ischemia.

Note that, whereas the techniques of FIG. 3 are preferably employed in "real time" based on IEGM signals as they are sensed, the technique can alternatively be employed based on previously recorded parameters. For example, IEGM data and posture change data may be collected over time then analyzed later to detect episodes of cardiac ischemia that have already occurred for the purpose of generate appropriate diagnostic data for physician review. Such delayed analysis techniques can be performed either using the implanted device itself or using an external data processing device based on data transmitted from the implanted device. Real time detection is preferred as it allows ischemia to be detected substantially immediately and appropriate warning signals to be promptly issued.

Change of Posture Detection

Turning now to FIGS. 5 and 6, exemplary techniques for detecting posture change based on IEGM signals will now be described. The techniques are broadly summarized in FIG. 5. At step 300, the pacer/ICD detects morphological features of IEGMs (or other appropriate cardiac electrical signals) that are affected by patient posture, such as PDI. At step 302, the pacer/ICD detects changes in patient posture based on transient variations in the morphological features, such as by detecting the transient variations in atrial PDI shown in FIG. 4. This IEGM-based detection procedure may be used in addition to accelerometer-based change of posture detection techniques within devices equipped with accelerometers. As such, the IEGM-based posture change detection procedure provides a technique for corroborating accelerometer-based posture change detection procedures. The IEGM-based procedure, for example, may be used to detect possible malfunctioning of the accelerometer. That is, if the IEGM-based technique consistently indicates that changes of posture are occurring but the accelerometer-based techniques do not, that might indicate that the accelerometer-based technique is no longer reliable, perhaps due to a malfunction within the accelerometer itself or within software used to process the accelerometer signals. Also, the IEGM-based technique may be advantageously used in any pacer/ICDs not equipped with accelerometer-based change of posture detection techniques or within devices where the accelerometer has malfunctioned.

FIG. 6 provides an example where atrial PDI is employed to detect posture change. Beginning at step 400, the pacer/ICD determines a running value of a baseline level of the atrial PDI, which may be, e.g., the running average or mean of the atrial PDI (as indicated by reference numeral 213 of FIG. 4.) At step 402, the pacer/ICD detects significant transient variations in atrial PDI, i.e. the pacer/ICD detects the sort of fluctuations occurring between minutes 12-15 of FIG. 4 that may be indicative of a change in posture. However, such transient variations may be the result of other circumstances (such as a sudden increase in patient activity without a change in posture) and so the presence of transient variations does not necessarily indicate a change in posture. Next, at step 404, the pacer/ICD detects a period of time (if any) during which the significant variations gradually subside, i.e. the pacer/ICD detects the sort of gradual decay exhibited during minutes 15-20 of FIG. 4. The presence of such a gradual decay is a further indication that a change of posture has occurred, as such gradual changes are often due to hemodynamic changes occurring as the cardiovascular system returns to an equilibrium state subject to a different gravitational vector due to the different posture. At step 406, the pacer/ICD determines the new baseline atrial PDI level following the significant variations in atrial PDI, which may again be the running average or mean of the atrial PDI (as indicated by reference numeral 215 of FIG. 4.) At step 408, the pacer/ICD indicates that a change in posture has occurred if the baseline atrial PDI level following the transient variations (215) differs significantly from the baseline level prior to the transient variations (213). In one example, the pacer/ICD determines that a change of posture has occurred by detecting (1) significant transient variations in PDI (caused by the movement of the patient from one posture to another), (2) a change in baseline PDI (caused by gravity-dependent and position-based hemodynamic and pulmonary affects associated with the new posture) and (3) a change in standard deviation of the PDI or peak-to-peak variability of the PDI (caused by gravity-dependent and position-based hemodynamic and pulmonary affects associated with the new posture). Transient variations without a corresponding change in baseline levels may instead be indicative of patient activity without a change in posture. Conversely, a change in baseline level without intervening transient variations may instead be indicative of a cardiac ischemia or other medical disorder. As noted, the detection of a change of posture is further indicated if the transient variations gradually subside. (Note that, at some point during clinical follow-up, a calibration can be performed, i.e. baseline and peak-to-peak changes in PDI in each body position can be noted versus each body position so that specific changes can be correlated to each body position, thereby providing an identification of the exact body position, not just the fact that a body position change has occurred.

At step 410, the pacer/ICD may further corroborate the change in posture based on changes in respiration, heart rate, blood pressure (as detected by an implanted blood pressure sensor), oxygen consumption (as detected by an implanted oxygen consumption sensor) or based on accelerometer output signals, if such detectors are so provided. As already noted, heart rate, blood pressure and oxygen consumption have been found to be affected by posture. Respiration detection techniques are discussed in, e.g., U.S. patent application Ser. No. 11/127,389, filed May 11, 2005, entitled "System and Method for Detection of Respiration Patterns via Intracardiac Electrogram Signals". Blood pressure detection techniques are discussed in, for example, U.S. patent application Ser. No. 11/378,604, of Kroll et al., filed Mar. 16, 2006, entitled "System and Method for Detecting Arterial Blood Pressure based on Aortic Electrical Resistance using an Implantable Medical Device". Oxygen consumption sensors are discussed in U.S. Pat. No. 6,016,443 to Ekwall, et al., entitled "Implantable Ischemia Detector and Implantable Stimulator Employing Same".

Finally, with regard to FIG. 6, although atrial PDI is a particularly effective metric for use in detecting changes in posture, other metrics or morphological parameters may instead be used. In particular, whereas the atrial PDI is derived from a paced atrial beat, a similar integral can be performed on the P-wave to derive the P-wave integral, which represents the morphology of the P-wave, and that varies along with the position. Similarly, integrals over the QRS (Intrinsic) and PDI over the V-pace, integral over the T-wave all will likely exhibit changes in peak-to-peak variability in morphology and/or baseline that correlate with the body position In some cases, some metrics may be more effective in identifying particular changes in posture. Otherwise conventional experimental techniques may be employed to identify particular morphological parameters most affected by particular changes in posture so as to optimize the specificity of the IEGM-based technique. Various different metrics or morphological parameters may be combined to further improve specificity. Techniques for combining different parameters into a single metric value for evaluation are set forth in U.S. patent application Ser. No. 10/339,989 to Koh et al., entitled "System and Method for Detecting Circadian States Using an Implantable Medical Device," filed Jan. 10, 2003.

What have been described are various techniques for detecting cardiac ischemia and changes in posture via IEGM signals and for delivering appropriate therapy. For the sake of completeness, a detailed description of an exemplary pacer/ICD for controlling these functions will now be provided. However, principles of invention may be implemented within other pacer/ICD implementations or within other devices.

Exemplary Pacemaker/ICD

FIG. 7 provides a simplified block diagram of the pacer/ICD, which is a multi-chamber stimulation device capable of treating both fast and slow arrhythmias with stimulation therapy, including cardioversion, defibrillation, and pacing stimulation (as well as capable of detecting cardiac ischemia and changes in posture and delivering appropriate therapy.) To provide atrial chamber pacing stimulation and sensing, pacer/ICD 10 is shown in electrical communication with a heart 512 by way of a left atrial lead 520 having an atrial tip electrode 522 and an atrial ring electrode 523 implanted in the atrial appendage. Pacer/ICD 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 524 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 524 is designed to receive atrial and ventricular cardiac signals and to deliver left ventricular pacing therapy using at least a left ventricular tip electrode 526, left atrial pacing therapy using at least a left atrial ring electrode 527, and shocking therapy using at least a left atrial coil electrode 528. With this configuration, biventricular pacing can be performed. Although only three leads are shown in FIG. 7, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 8:
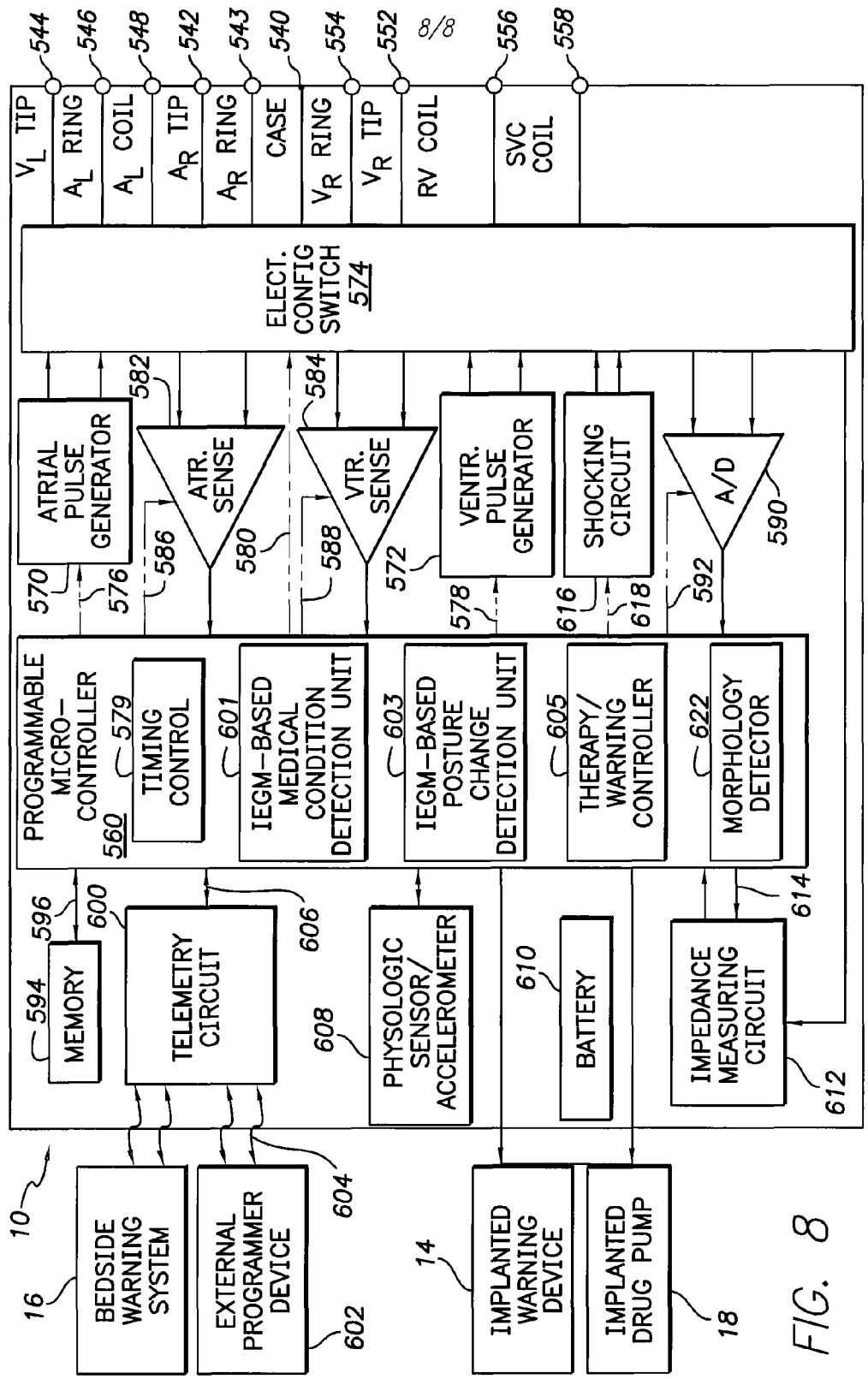
FIG. 8 is a functional block diagram of the pacer/ICD of FIG. 7, illustrating basic circuit elements that provide cardioversion, defibrillation and/or pacing stimulation in four chambers of the heart and particularly illustrating an IEGM-based ischemia detector and an IEGM-based posture change detector.

A simplified block diagram of internal components of pacer/ICD 10 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 540 for pacer/ICD 10, shown schematically in FIG. 8, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 543. To achieve left chamber sensing, pacing and shocking, the connector includes at least a left ventricular tip terminal ($V_L$ TIP) 544, a left atrial ring terminal ($A_L$ RING) 546, and a left atrial shocking terminal ($A_L$ COIL) 548, which are adapted for connection to the left ventricular ring electrode 526, the left atrial tip electrode 527, and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558, which are adapted for connection to the right ventricular tip electrode 532, right ventricular ring electrode 534, the RV coil electrode 536, and the SVC coil electrode 538, respectively. Separate terminals (not shown) may be provided for connecting the implanted warning device 14 and the implanted drug pump 18, which are instead shown coupled directly to internal functional components of the pacer/ICD that control these devices.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 8, an atrial pulse generator 570 and a ventricular/impedance pulse generator 572 generate pacing stimulation pulses for delivery by the right atrial lead 520, the right ventricular lead 530, and/or the coronary sinus lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, coronary sinus lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the coronary sinus lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 602, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 602 through an established communication link 604. Pacer/ICD 10 further includes an accelerometer or other physiologic sensor 608, commonly referred to as a "rate-responsive" sensor because it is typically used to adjust pacing stimulation rate according to the exercise state of the patient. However, the physiological sensor 608 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV Delay, V-V Delay, etc.) at which the atrial and ventricular pulse generators, 570 and 572, generate stimulation pulses. While shown as being included within pacer/ICD 10, it is to be understood that the sensor 608 may also be external to pacer/ICD 10, yet still be implanted within or carried by the patient. A common type of rate responsive sensor is an activity sensor incorporating an accelerometer or a piezoelectric crystal, which is mounted within the housing 540 of pacer/ICD 10. Other types of physiologic sensors are also known, for example, sensors that sense the oxygen content of blood, respiration rate and/or minute ventilation, pH of blood, ventricular gradient, etc. The accelerometer is preferably a 3D accelerometer equipped to provide signals for use in detecting changes in posture.

The pacer/ICD additionally includes a battery 610, which provides operating power to all of the circuits shown in FIG. 8. The battery 610 may vary depending on the capabilities of pacer/ICD 10. If the system only provides low voltage therapy, a lithium iodine or lithium copper fluoride cell may be utilized. For pacer/ICD 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 8, pacer/ICD 10 is shown as having an impedance measuring circuit 612 which is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 64 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Microcontroller 50 also includes an IEGM-based medical condition detection unit 601 for detecting a medical condition, such as cardiac ischemia, while taking into account changes in posture in accordance with the technique described above in connection with FIGS. 2-4. Posture may be detected via accelerometer 608 or via an IEGM-based posture change detection unit 603 in accordance with the technique described above in connection with FIGS. 5-6. A therapy/warning controller 605 is also provided for controlling delivery of therapy and or warning signals based on the output of IEGM-based medical condition detection unit 601 and IEGM-based posture change detection unit 603. Depending upon the implementation, the various components may be implemented as separate software modules. However, the modules may be combined so as to permit single modules to perform multiple functions.

What have been described are various exemplary systems and methods for use with an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the scope of the invention. Note also that the term "including" as used herein is intended to be inclusive, i.e. "including but not limited to".

What is claimed is:

1. A method for use with an implantable medical device for detecting changes in posture in a patient in which the device is implanted, comprising: sensing an electrical cardiac signal within the patient using the device;
    obtaining atrial paced depolarization integral (PDI) measurements of the cardiac signal affected by one or more of patient posture, patient activity and cardiac ischemia;
    determining an atrial PDI baseline level corresponding to a first posture of a patient;
    detecting for a significant transient variation period in atrial PDI measurements during which the peak-to-peak values of the PDI measurements fluctuate between two to three times the peak-to-peak values of the atrial PDI measurements defining the first posture atrial PDI baseline level;
    detecting for a transient decay period subsequent to a significant transient variation period during which the transient PDI measurements gradually decay to a subsequent baseline atrial PDI corresponding to a second posture of the patient;
    detecting, using a microprocessor, a significant change in patient posture when the significant transient variation period is detected, the transient decay period is detected and a difference between the initial atrial PDI baseline and the subsequent atrial PDI baseline exceeds a predetermined threshold indicative of a significant posture change; and
    detecting, using the microprocessor, patient activity without a significant change in posture when the significant transient variation period is detected and the difference between the initial atrial PDI baseline and the subsequent atrial PDI baseline does not exceed the predetermined threshold.

2. The method of claim 1 further including controlling at least one device function based on the determination of a change in posture.

3. The method of claim 2 wherein the at least one device function includes controlling a pacing rate in response to a change in posture.

4. The method of claim 1 further comprising:
    detecting variations in electrical cardiac signals indicative of a possible episode of a medical condition; and
    detecting an episode of the medical condition based on the variations in the cardiac signals while distinguishing variations due to changes in posture.

5. The method of claim 4 wherein the medical condition is cardiac ischemia.

6. The method of claim 5 wherein detecting variations in the cardiac signals indicative of a possible episode of a cardiac ischemia includes detecting selected variations in one or more of the elevation, width, maximum slope, and peak amplitude of P-waves, QRS-complexes, T-waves and intervals therebetween.

7. The method of claim 6 wherein detecting selected variations in the cardiac signals includes detecting variations in an ST-segment elevation.

8. The method of claim 5 further including the step of controlling therapy in response to the detection of an episode of cardiac ischemia.

9. The method of claim 5 further including the step of generating a warning signal in response to detection of an episode of a medical condition.

10. The method of claim 1 wherein the baseline levels are represented by one or more of a standard deviation in the PDI or a peak-to-peak variability in the PDI.

11. The method of claim 1 wherein the baseline levels are represented by one or more of an average or a mean PDI level.

12. The method of claim 1 further including
    detecting a posture change corroborating parameter including one or more of heart rate, blood pressure and oxygen consumption; and
    corroborating the determination that a change in posture occurred using the corroborating parameter.

13. The method of claim 1 wherein the difference between the initial atrial PDI baseline and the subsequent atrial PDI baseline corresponds to a change in mean atrial PDI.

14. The method of claim 1 wherein the difference between the initial atrial PDI baseline and the subsequent atrial PDI baseline corresponds to a change in standard deviation of atrial PDI.

15. A system for use with an implantable medical device for implant within a patient, comprising:
    a cardiac signal detection unit configured to sense an electrical cardiac signal within the patient and to obtain atrial paced depolarization integral (PDI) measurements of the cardiac signal affected by one or more of patient posture, patient activity and cardiac ischemia from the cardiac signal; and a posture change detection unit configured to determine an atrial PDI baseline level corresponding to a first posture of a patient, to detect for a significant transient variation period in the atrial PDI measurements during which the peak-to-peak values of the PDI measurements fluctuate between two to three times the peak-to-peak values of the atrial PDI measurements defining the first-posture atrial PDI baseline level, to detect for a transient decay period subsequent to a significant transient variation period during which the transient PDI measurements gradually decay to a subsequent baseline atrial PDI corresponding to a second posture of the patient, to detect a significant change in patient posture when the significant transient variation period is detected, the transient decay period is detected and a difference between the initial atrial PDI baseline and the subsequent atrial PDI baseline exceeds a predetermined threshold indicative of a significant posture change, and to detect patient activity without a significant change in posture when the significant transient variation period is detected and the difference between the initial atrial PDI baseline and the subsequent atrial PDI baseline does not exceed the predetermined threshold.

16. A system for use with an implantable medical device for implant within a patient, comprising:

means for sensing an intracardiac electrogram (IEGM) signal within the patient; means for obtaining atrial paced depolarization integral (PDI) measurements of the cardiac signal affected by one or more of patient posture, patient activity and cardiac ischemia from the IEGM;

means for determining an atrial PDI baseline level corresponding to a first posture of a patient;

means for detecting for a significant transient variation in atrial PDI measurements during which the peak-to-peak values of the PDI measurements fluctuate between two to three times the peak-to-peak values of the atrial PDI measurements defining the first-posture atrial PDI baseline level;

means for detecting for a transient decay period subsequent to a significant transient variation period during which the transient PDI measurements gradually decay to a subsequent baseline atrial PDI corresponding to a second posture of the patient;

means for detecting a significant change in patient posture when the significant transient variation period is detected, the transient decay period is detected and a difference between the initial atrial PDI baseline and the subsequent atrial PDI baseline exceeds a predetermined threshold indicative of a significant posture change; and means for detecting patient activity without a significant change in posture when the significant transient variation period is detected and the difference between the initial atrial PDI baseline and the subsequent atrial PDI baseline does not exceed the predetermined threshold.

\* \* \* \* \*